(12) United States Patent
Schwarz

(10) Patent No.: US 11,052,071 B2
(45) Date of Patent: Jul. 6, 2021

(54) ORAL DOSAGE FORM COMPRISING RIFAXIMIN IN FORM BETA

(71) Applicant: Sandoz AG, Basel (CH)

(72) Inventor: Franz Xaver Schwarz, Kundl/Tirol (AT)

(73) Assignee: Sandoz AG, Basel (CH)

( * ) Notice: Subject to any disclaimer, the term of this patent is extended or adjusted under 35 U.S.C. 154(b) by 384 days.

(21) Appl. No.: 16/076,772

(22) PCT Filed: Apr. 25, 2018

(86) PCT No.: PCT/EP2018/060547
§ 371 (c)(1),
(2) Date: Aug. 9, 2018

(87) PCT Pub. No.: WO2018/197538
PCT Pub. Date: Nov. 1, 2018

(65) Prior Publication Data
US 2019/0388404 A1 Dec. 26, 2019

(30) Foreign Application Priority Data

Apr. 26, 2017 (EP) ..................................... 17168281

(51) Int. Cl.
*A61K 31/437* (2006.01)
*A61K 9/00* (2006.01)
*A61K 9/20* (2006.01)

(52) U.S. Cl.
CPC .......... *A61K 31/437* (2013.01); *A61K 9/0053* (2013.01); *A61K 9/2009* (2013.01); *A61K 9/2054* (2013.01); *A61K 9/2059* (2013.01); *A61K 9/2095* (2013.01)

(58) Field of Classification Search
None
See application file for complete search history.

(56) References Cited

U.S. PATENT DOCUMENTS

| 7,045,620 B2 * | 5/2006 | Viscomi |
| 2008/0262220 A1 | 10/2008 | Viscomi et al. |
| 2011/0065740 A1 | 3/2011 | Forbes et al. |

FOREIGN PATENT DOCUMENTS

| CN | 103340856 A | 10/2013 |
| EP | 1557421 A1 | 7/2005 |
| EP | 1698630 B1 | 9/2014 |
| WO | 2005044823 A2 | 5/2005 |
| WO | 2006094737 A2 | 9/2006 |
| WO | 2008029208 A1 | 3/2008 |
| WO | 2009137672 A1 | 11/2009 |
| WO | 2012038898 A1 | 3/2012 |
| WO | 2014091432 A1 | 6/2014 |

OTHER PUBLICATIONS

Guslandi, "Rifaximin in the treatment of inflammatory bowel disease", World J Gastroenterol, 2011, vol. 17(42), pp. 4643-4646.*
International Search Report and Written Opinion for PCT/EP2018/060547, dated Jul. 12, 2018, 16 pages.
Viscomi, G.C., et al., Crystal forms of rifaximin and their effect on pharmaceutical properties, CrystEngComm, The Royal Society of Chemistry, 2008, vol. 10, pp. 1074-1081.

* cited by examiner

*Primary Examiner* — Savitha M Rao
*Assistant Examiner* — Gregg Polansky
(74) *Attorney, Agent, or Firm* — Luedeka Neely Group, P.C.

(57) ABSTRACT

The present invention relates to an oral dosage form containing rifaximin in form beta, wherein the oral dosage form provides delayed release of the active pharmaceutical agent. Further, the invention relates to the preparation of an oral dosage form, preferably a tablet.

9 Claims, 4 Drawing Sheets

ORAL DOSAGE FORM COMPRISING RIFAXIMIN IN FORM BETA

This application is a Section 371 national phase entry of PCT application PCT/EP2018/060547, filed Apr. 25, 2018. This application also claims the benefit of the earlier filing date of European patent application 17168281.8, filed Apr. 26, 2017.

The present invention relates to an oral dosage form containing rifaximin in form beta, wherein the oral dosage form provides delayed release of the active pharmaceutical agent. Further, the invention relates to the preparation of an oral dosage form, preferably a tablet.

BACKGROUND OF THE INVENTION

Rifaximin is a semisynthetic derivate of rifamycin, wherein rifaximin is an oral, bactericidal broad-spectrum antibiotic. The IUPAC name of rifaximin is (2S,16Z,18E,20S,21S,22R,23R,24R,25S,26S,27S,28E)-5,6,21,23,25-pentahydroxy-27-methoxy-2,4,11,16,20,22,24,26-octamethyl-2,7-(epoxypenta-deca[1,11,13]trienimino) benzofuro[4,5-e]pyrido[1,2-a]-benzimida-zole-1,15(2H)-dione,25-acetate and the compound is represented by the following formula

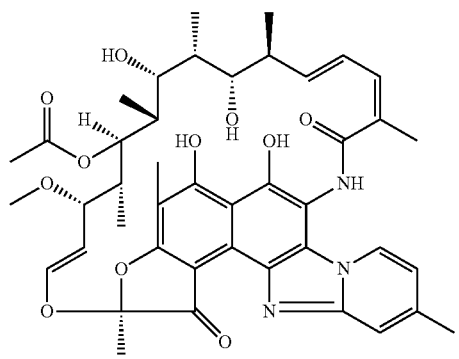

Rifaximin is reported to be poorly absorbed systemically, i.e. in the bloodstream, and as a consequence it shows its efficiency almost exclusively in the intestinal lumen.

Rifaximin can be used in the treatment of bacterial infections of the gastrointestinal tract, for example, in the treatment of traveler's diarrhea. In addition, the active pharmaceutical agent can be used in the treatment of Crohn's disease. Crohn's disease which is also referred to as Morbus Crohn is a type of inflammatory disease that may affect the whole gastrointestinal tract. In particular Morbus Crohn is regraded to belong to the group of chronic inflammatory bowel diseases wherein these diseases are reported to be inter alia caused by bacterial infections.

The treatment of Crohn's disease requires a high dose of rifaximin. Further, the active pharmaceutical agent should be provided in a form having a low solubility and bioavailability for the best efficacy.

Up to now more than 10 polymorphic forms of rifaximin have been described in the art. Many of these polymorphic forms can convert into each other. For example, EP 1 557 421 A1 describes the conversion of the β form into the α form and EP 1 698 630 discloses that the δ polymorph can convert to the ε polymorph. Rifaximin in form α is a widely used form, inter alia in a tablet marketed under the tradename Xifaxan. The form α of rifaximin is reported to show an increased initial solubility, especially under acidic conditions such as in the stomach. To reduce said solubility before the pharmaceutical agent reaches its site of action, the colon, WO 2006/094737 A2 discloses a rifaximin preparation in gastro-resistant microgranules. According to the document, rifaximin is provided with an enteric coating of methacrylic acid/ethyl acrylate copolymer (Kollicoat® MAE 100 P) which is reported to dissolve and thereby releasing the pharmaceutical agent under conditions only in the intestinal tract. The weight of the enteric coating is about 30% of the used amount of the pharmaceutical agent. Thus, also in view of further pharmaceutical excipients an oral dosage form, such as tablet, treated with enteric material in that way and comprising 400 mg of rifaximin has a weight of above 700 mg. To administer the dose of 800 mg of rifaximin, which is required for the treatment of Crohn's disease, two doses (tablets) of 400 mg have to be delivered. Such a dosage regime may lead to a poor patient compliance.

Thus, there is a need for a high strength oral dosage form containing rifaximin, wherein the rifaximin exhibits a low solubility of the API, especially under acidic conditions such as in the stomach. Hence, it was an object of the present invention to overcome the drawbacks of the above-mentioned prior art.

In particular, it was an object of the present invention to provide a high strength oral dosage form containing rifaximin in a form being substantially not soluble in the stomach, the dosage form being suitable for the treatment of inflammatory diseases of the gastrointestinal tract, in particular in the treatment of Crohn's disease by a once daily administration. Further, an oral dosage form with good workability should be provided. Still further it was an object to provide a delayed release oral dosage form containing rifaximin having reduced amounts of excipients.

According to the present invention, the above objects have unexpectedly been achieved by an oral dosage form comprising a specific polymorphic form of rifaximin in a specific amount calculated on the basis of anhydrous rifaximin, wherein the oral dosage form does not comprise or is substantially free of enteric release material.

Thus, a subject of the invention is an oral dosage form for delayed release comprising
(A) rifaximin in polymorphic form β, and
(B) optionally one or more pharmaceutical excipient(s),
wherein the rifaximin (A) contains 700 to 900 mg, preferably 800 mg rifaximin calculated on the basis of anhydrous rifaximin, and
wherein the oral dosage form does not comprise an enteric release coating.

A further subject of the present invention is a method for preparing an oral dosage form according to the invention comprising the steps of
(i) providing (A) rifaximin in polymorphic form β and (B) optionally one or more pharmaceutical excipient(s)
(ii) granulating the mixture from step (i)
(iii) compressing the mixture from step (i) or the granulates from step (ii) and optionally further pharmaceutical excipient(s) to a tablet or filing the mixture from step (i) or the granulates from step (ii) and optionally further excipients into a capsule, and
(iv) optionally coating the tablet from step (iii) with a non-enteric coating.

In the art it is known that rifaximin in form α and rifaximin in form ß have a quite similar solubility. However, it was now unexpectedly found that when preparing a delayed release dosage form beta can be advantageously used. Contrary to form alpha an enteric-coating is not necessary.

DETAILED DESCRIPTION OF THE INVENTION

The present invention relates to an oral dosage form for delayed release comprising (A) rifaximin in polymorphic form β, and (B) optionally one or more further pharmaceutical excipient(s), wherein the rifaximin (A) is present in an amount of 700-900 mg, preferably 800 mg rifaximin calculated on the basis of anhydrous rifaximin, and wherein the oral dosage form does not comprise an enteric release coating.

In a preferred embodiment, the oral dosage form of the present invention is a dosage form for a once daily administration, in particular for a once daily administration of a rifaximin dose suitable for the treatment of inflammatory bowel diseases, e.g. Crohn's disease.

The oral dosage form of the present invention is an oral dosage form for delayed release of the active pharmaceutical ingredient. Generally, the term "delayed release" indicates that the rifaximin is not released immediately following administration but at a later time. Hence, an oral dosage form having delayed release can be understood as being a dosage form not showing immediate release (i.e. a release of at least 70% of the active ingredient within one hour).

In a preferred embodiment the oral dosage form releases the active pharmaceutical ingredient after having passed the acidic conditions of the stomach. In particular the oral dosage form of the present invention releases less than 10% of the active ingredient until having passed the stomach.

In a preferred embodiment the oral dosage form releases less than 10%, preferably less than 5% and in particular less than 2% of the active ingredient within 120 minutes. Further, it is preferred that the oral dosage form releases more than 10%, preferably more than 25%, in particular more than 50% within 150 minutes and/or more than 20%, preferably more than 50% and in particular more than 85% within 180 minutes.

The release is determined according to USP, item 711 Dissolution (Apparatus 2, Method A, 37.5° C.±0.5° C., 100 rpm; 120 minutes 0.1 N HCl and after 2 hours a phosphate buffer with 2% of sodium lauryl sulfate is added to bring up the pH to 6.8.

As indicated above, rifaximin can be present in different polymorphic forms. These polymorphic forms can be different crystalline forms and/or the result of stoichiometric and non-stoichiometric hydration or solvation.

A polymorphic form can be represented by one or more, preferably at least three, specific diffraction peaks in X-ray powder diffraction (XRPD).

In the present application, the XRPD is measured as described below in the experimental section.

Further, unless indicated otherwise, XRPD peaks are reported as degrees 2θ values with a standard error of ±0.2 degrees 2θ.

Figure 1:
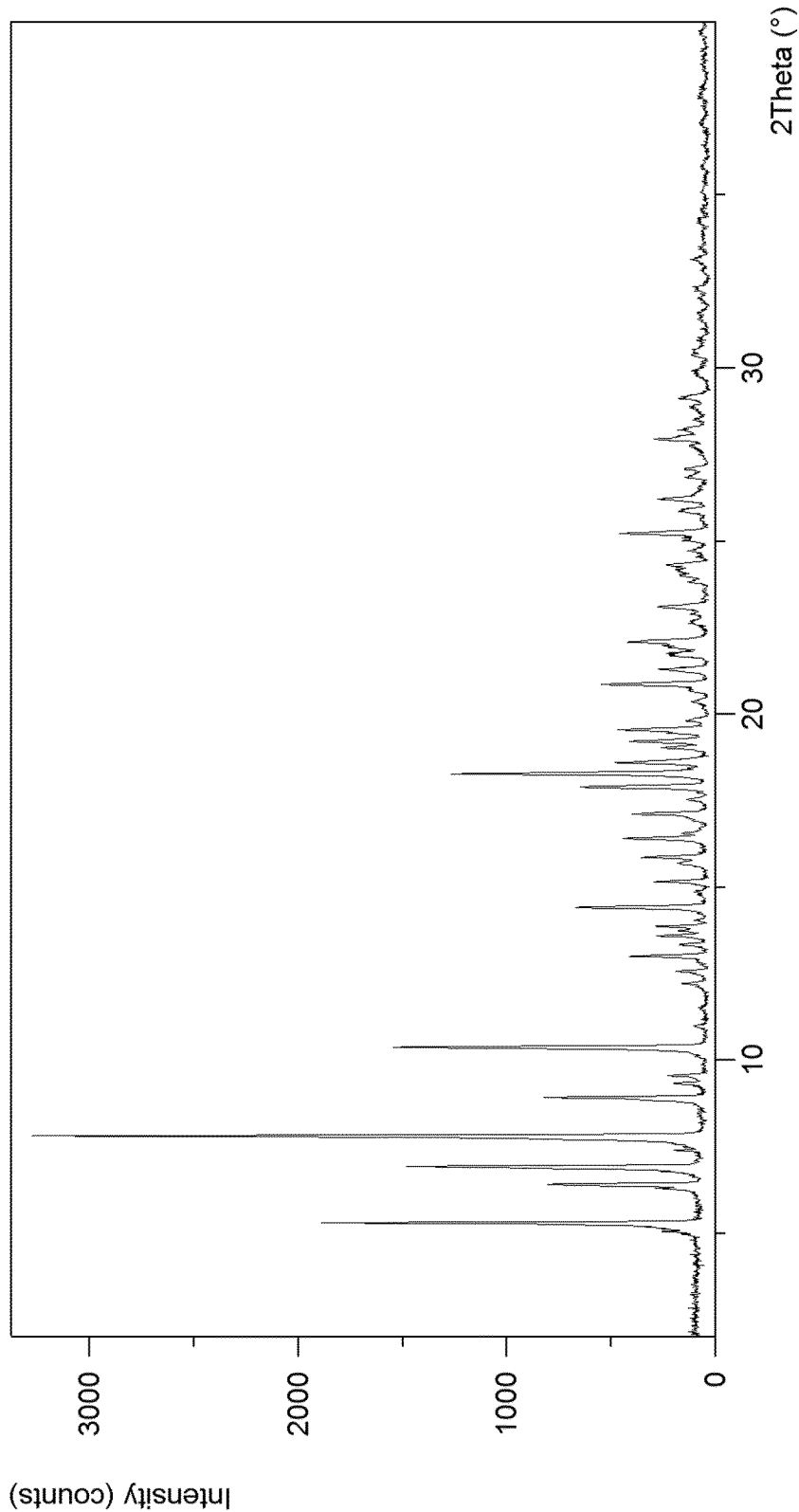
FIG. 1: XRPD of rifaximin in form β

Component (A) of the present application is rifaximin in polymorphic form β having diffraction peaks in the XRPD at 5.3, 6.9, 7.8, 10.4, 14.4 and 18.3 degrees 2θ (±0.2 degrees 2θ). These peaks may be regarded as particularly characteristic diffraction peaks for rifaximin in polymorphic form β. Preferably further peaks occur at 6.4, 8.9, 9.3, 9.5, 12.2, 12.6, 13.0, 13.6, 13.9, 15.1, 15.8, 16.4, 17.1, 17.9, 18.6, 19.0, 19.2, 19.5, 20.8, 21.3, 21.7, 22.1, 23.1, 24.3, 25.2, 26.2 and/or 27.9 degrees 2θ (±0.2 degrees 2θ). A respective XRPD of form β is shown in FIG. 1.

The oral dosage form of the present invention comprises rifaximin in form β, preferably pure form β. In other words, the oral dosage form does preferably not comprise other polymorphic forms of rifaximin.

In a preferred embodiment the oral dosage form is "essentially free" of rifaximin in polymorphic forms α and δ. In an especially preferred embodiment the present oral dosage form contains rifaximin in polymorphic form β in an amount of more than 98.5%, preferably more than 99%, in particular more than 99.5%, based on the amount of rifaximin.

Figure 2:
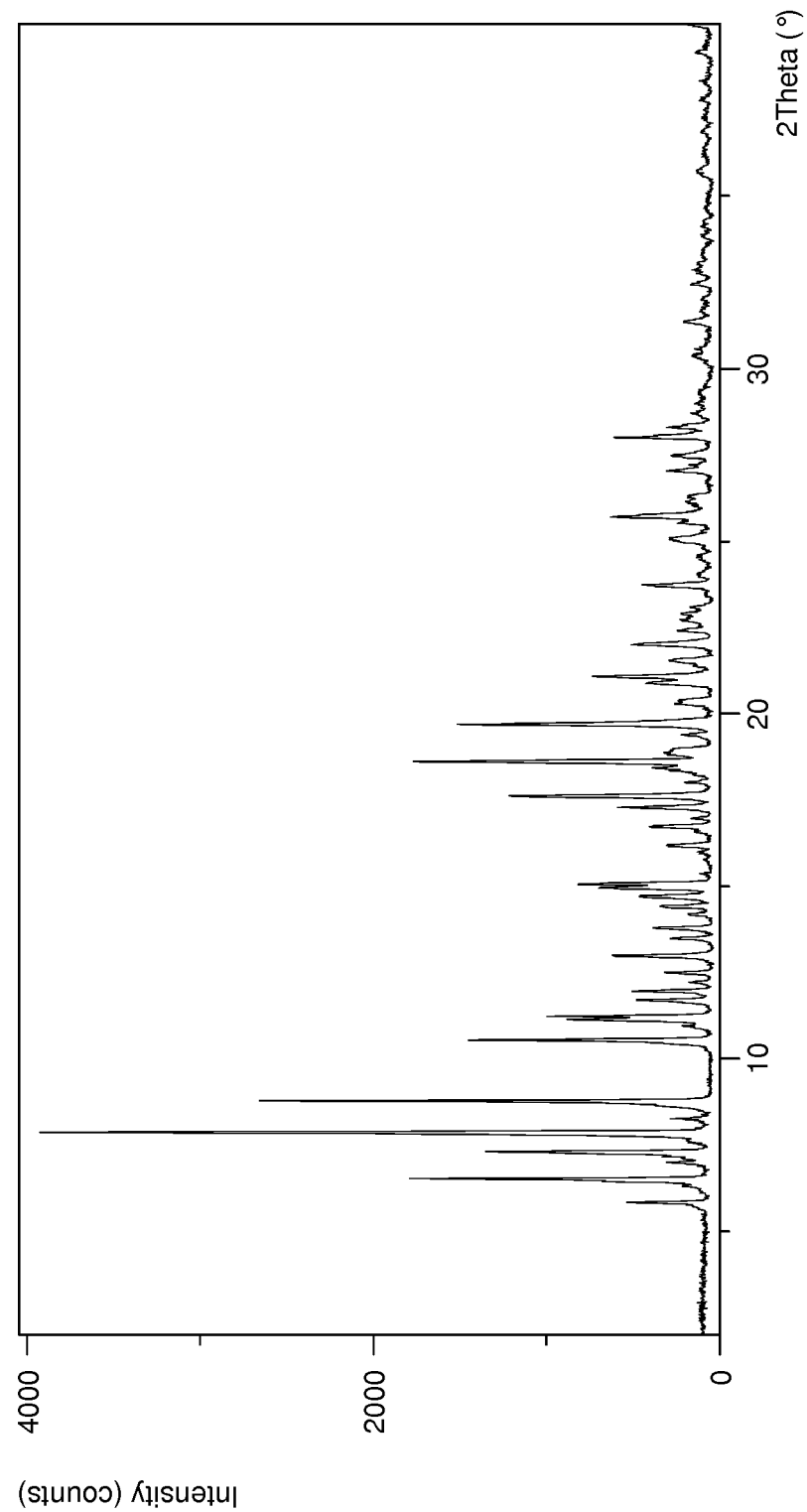
FIG. 2: XRPD of rifaximin in form α

Rifaximin in polymorphic form α is characterized in having diffraction peaks in the XRPD at 11.7, 13.0, and 19.6 degrees 2θ (±0.2 degrees 2θ). Further peaks occur at 6.5, 7.3, 7.9, 8.7 10.5, 11.1, 17.6, 18.6, 21.1, 21.5 and/or 22.0 degrees 2θ (±0.2 degrees 2θ). A respective XRPD of form α is shown in FIG. 2.

Figure 3:
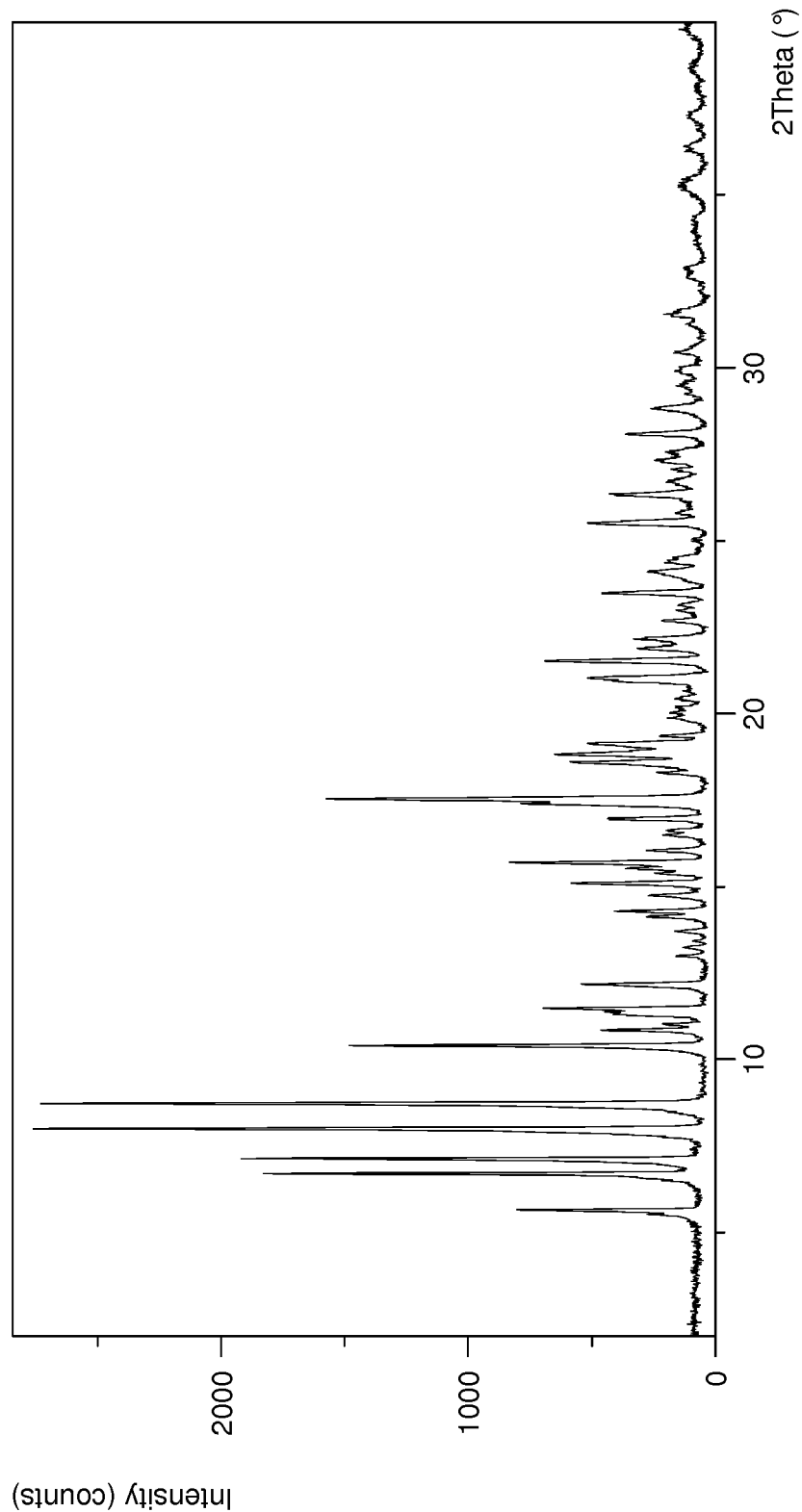
FIG. 3: XRPD of rifaximin in form δ

Rifaximin in polymorphic form δ is represented as having diffraction peaks in the XRPD at 5.6, 12.2 and 17.0 degrees 2θ (±0.2 degrees 2θ). Further peaks can occur at 6.7, 7.1, 8.0, 8.7 10.4, 10.8, 11.3, 17.4, 17.5, 18.6, 18.8, 19.1, 21.0 and/or 21.5 degrees 2θ (±0.2 degrees 2θ). A respective XRPD of form δ is shown in FIG. 3.

In another preferred embodiment of the invention, the oral dosage form is "essentially free" of other polymorphic forms of rifaximin, such as amorphous rifaximin and rifaximin in polymorphic forms α, δ and ε.

The term "essentially free" usually means that, apart from rifaximin in form β, the other polymorphic forms of rifaximin are present in such a low amount that they do not have a clinically significant influence on the bioavailability. Alternatively, the term "essentially free" usually means that the other polymorphic forms are present in such a low amount that they cannot be found in the XRPD. In other words, in a preferred embodiment the drug of the oral dosage form of the present invention only shows XRPD peaks which relate to rifaximin in form β. Consequently, component (A) can be regarded as pure rifaximin in polymorphic form β.

In a preferred embodiment the oral dosage form of the present invention, apart from rifaximin in polymorphic form β, comprises other polymorphic form(s) of rifaximin in an amount of less than 5 mol %, more preferably less than 3 mol %, based on the total molar amount of rifaximin. In particular, the oral dosage form of the present invention comprises less than 5 mol %, more preferably less than 3 mol %, in particular less than 1 mol %, of rifaximin in polymorphic form α or in polymorphic form δ.

The molar ratio of polymorphs can preferably be determined by the "Rietveld Analysis" of powder X-ray diffraction data, wherein the diffraction data are obtained as described below in the experimental section.

In a preferred embodiment of the invention component (A), rifaximin in polymorphic form β, can have a water content of 3.0 to 20.0 wt %, more preferably 6.5 to 15.0 wt %, even more preferably 8.0 to 12.0 wt %, in particular 9.0 to 10.0 wt %, especially about 9.2 wt %.

As used herein, the term "about" means within a statistically meaningful range of a value. Such a range can be within an order of magnitude, typically within 10%, more typically within 5%, even more typically within 1% and most typically within 0.1% of the indicated value or range. Sometimes, such a range can lie within the experimental error, typical of standard methods used for the measurement and/or determination of a given value or range.

Further, component (A), rifaximin in polymorphic form β, contains 700-900 mg, preferably 800 mg rifaximin calculated on the basis of anhydrous rifaximin.

The term "anhydrous" as used herein, refers to a solid wherein no water is coordinated in or accommodated by the crystal structure. However, an anhydrate or a solid in anhydrous form may still comprise residual water due to surface adsorption, solvent inclusions and/or absorption in disordered regions.

Under the proviso that the oral dosage form contains 800 mg rifaximin calculated on the basis of anhydrous rifaximin, the amount of rifaximin in form β having a water content of x wt. % can be calculated by the following formula $$\text{Amount rifaximin } \beta = 800 \text{ mg} \times \frac{1}{1-\frac{x}{100}}$$

Thus, for example rifaximin in form β having a water content of 10 wt % has to be comprised in the present oral dosage form in an amount of 888.89 mg to contain 800 mg rifaximin calculated on the basis of anhydrous rifaximin.

It is further preferred that component (A), rifaximin in form β, can be present in form of a powder or granules.

It is preferred that rifaximin (A) in form of a powder can preferably have an average particle size between 10 μm and 50 μm, preferably between 15 μm and 45 μm.

It is alternatively preferred that rifaximin (A) in form of granules can preferably have an average particle size between 1 μm and 100 μm, preferably between 5 μm and 90 μm.

The term "average particle size" refers to the volume average particle size ($D_{50}$), which can be determined by the light scattering method using a Mastersizer 2000 apparatus made by Malvem Instruments (wet measurement, paraffin as dispersant, 2000 rpm, ultrasonic waves for 60 sec., data interpretation via Fraunhofer method).

Further, the granules can preferably be substantially free of an enteric release material or enteric release coating.

In a preferred embodiment the oral dosage form of the invention can have a drug load (amount of the active pharmaceutical ingredient) of more than 40%. It is preferred that the oral dosage form of the present invention can comprise 60 to 95 wt % of rifaximin (A), more preferably 65 to 90 wt % of rifaximin (A), in particular 70 to 85 wt % of rifaximin (A). As far as compound (A), rifaximin in form β, is concerned the same applies as defined above. Further, the oral dosage form can preferably be free of excipients which may act as enteric release material or enteric release coating.

The oral dosage form of the present invention can preferably further comprise one or more further pharmaceutical excipient(s). Suitbale pharmaceutical excipients are for example disclosed in "Lexikon der Hilfsstoffe für Pharmazie, Kosmetik und angrenzende Gebiete", published by H. P. Fielder, 4$^{th}$ Edition, and "Handbook of Pharmaceutical Excipients", 3$^{rd}$ Edition, published by A. H. Kibbe, American Pharmaceutical Association, Washington, USA, and Pharmaceutical Press, London. Generally, there are no specific restrictions concerning the chemical nature of these excipients provided that the excipient(s) comprised in the oral dosage form is/are pharmaceutically acceptable. A pharmaceutically acceptable excipient is an excipient which is relatively non-toxic and innocuous to a patient at concentrations consistent with the effective activity of the rifaximin in polymorphic form β so that any side effects ascribable to the excipient do not vitiate the beneficial effects of rifaximin in polymorphic form β.

Therefore, according to the present invention, pharmaceutical excipients are for example fillers, binders, disintegrants, glidants, coating materials, sweeteners, flavoring agents, and coloring agents such as for example pigments. Other excipients known in the field of pharmaceutical compositions/oral dosage forms may also be used. In a preferred embodiment, the composition of the invention is substantially free, preferably completely free, of an excipient which may act as an enteric release coating.

Fillers can be used to increase the bulk volume and weight of a low-dose drug to a limit at which a pharmaceutical dosage form can be formed. Fillers may fulfil several requirements, such as being chemically inert, non-hygroscopic and biocompatible.

Examples of fillers according to the present invention include, but are not limited to, kaolin, microcrystalline cellulose, silicated microcrystalline cellulose, lactose, such as anhydrous lactose or lactose monohydrate form, sugars, such as dextrose, maltose, saccharose, glucose, fructose or maltodextrine, sugar alcohols, such as mannitol, maltitol, sorbitol, xylitol, powdered cellulose and starch. Fillers can preferably be present from 5-30 wt %, more preferably from 12-28 wt %, in particular from 15-25 wt %, based on the total weight of the oral dosage form.

Binders ensure that tablets and granules can be formed with the required mechanical strength, and give volume to low active dose tablets. Binders can be present in an amount of 0 to 15 wt %, preferably in an amount of 3 to 10 wt % based on the total weight of the oral dosage form. Suitable binders according to the present invention include, but are not limited to, hydroxypropyl cellulose, hypromellose (hydroxypropyl methylcellulose, HPMC), acacia, alginic acid, carboxymethyl cellulose, ethyl cellulose, methylcellulose, hydroxyethyl cellulose, ethylhydroxyethyl cellulose, polyvinyl alcohol, polyacrylates, carboxymethyl cellulose calcium, carboxymethyl cellulose sodium, compressible sugar, ethyl cellulose, gelatin, liquid glucose, methylcellulose, polyvinyl pyrrolidone and pregelatinized starch. In an alternative preferred embodiment the oral dosage form of the present invention does not comprise a binder.

Disintegrants are compounds which enhance the ability of the dosage form, preferably the ability of the tablet, to break into smaller fragments when in contact with a liquid, preferably water. Disintegrants can be present for example in an amount of 0 to 10 wt %, preferably in an amount of 0.25 to 85 wt % in particular in an amount of 0.5 to 5 wt % based on the total weight of the oral dosage form. Suitable disintegrants according to the present invention include, but are not limited to, carboxymethyl cellulose calcium, carboxymethyl cellulose sodium, croscarmellose (crosslinked carboxymethyl cellulose) sodium, cross-linked polyvinylpyrrolidone, crospovidone (cross-linked povidone, a synthetic cross-linked homopolymer of N-vinyl-2-pyrrolidone), alginic acid, microcrystalline cellulose (such as refined wood pulp derived from alpha cellulose), hydroxypropyl cellulose, low substituted hydroxypropyl cellulose, polacrillin potassium, sodium alginate, sodium starch glycolate, partially hydrolysed starch, sodium carboxymethyl starch, and starch.

Lubricants generally can be regarded as substances which are suitable to reduce friction, such as static friction, sliding friction and rolling friction. In particular, lubricants reduce the shearing forces occurring on the borderline between tablet and mould, especially the sliding friction found during tablet pressing between the punch moving up and down in the die and the die wall on the one hand and between the edge of the tablet and the die wall on the other hand. Lubricants can be present for example in an amount of 0 to 5 wt %, preferably 0.5-4 wt %, in particular 0.75-3 wt %, based on the total weight of the oral dosage form. Suitable lubricants according to the present invention include, but are not limited to, calcium stearate, magnesium stearate, mineral oil, stearic acid, fumaric acid, sodium stearyl fumarate, zinc stearate and polyethylene glycol, in particular magnesium stearate.

Glidants can be used to improve the flowability. Suitable glidants are for example colloidal silicon dioxide, talcum or mixtures thereof. Glidants can be present in an amount of 0 to 5 wt %, preferably 0.5-4 wt % glidant, in particular 0.75-3 wt % glidant, based on the total weight of the oral dosage form.

The coating materials according to the present invention do not contain enteric release materials. Such coating materials are known in the art. An example of coating material for forming a coating film wherein the film does not affect the release of the API is Opadry II.

Suitable coloring agents according to the present invention include, but are not limited to, pigments, inorganic pigments, FD&C Red No. 3, FD&C Red No. 20, FD&C Yellow No. 6, FD&C Blue No. 2, D&C Green No. 5, D&C Orange No. 5, D&C Red No. 8, caramel, ferric oxide red, ferric oxide yellow and titanium dioxide.

The skilled person will appreciate that depending on formulation context and concentration a particular excipient can fulfill various and sometimes even different functions. For example, microcrystalline cellulose is a particularly hydrolyzed cellulose, which can be used as a filler, binder and/or disintegrating material in tablet production, dependent on formulation context and concentration. Reference is made to the literature on pharmaceutical excipients and pharmaceutical formulation, such as Fiedler—Encyclopedia of Excipients for Pharmaceuticals, Cosmetics and Related Areas, Wissenschaftliche Verlagsgesellschaft Stuttgart, 2013, Bauer, Frömming and Führer, "Lehrbuch der Pharmazeutischen Technologie", Wissenschaftliche Verlagsgesellschaft Stuttgart, 9. Auflage (2012) or, with a particular focus on tablet production, Augsburger and Stephen, Pharmaceutical Dosage Forms: Tablets, Third Edition, Volume 2, Informa Healthcare (2008). The skilled person will therefore appreciate that terms like "disintegrant", "binder", "lubricant", "filler", "plasticizer", "surfactant", "wetting agent", "film-forming agent", "coating material", "sweetener", "flavoring agent" and "coloring agent" are primarily functional definitions and that the structural characterization provided above are given so as to more easily allow identification of suitable excipients.

Further, the oral dosage form of the present invention preferably does not comprise an enteric release coating. More preferably, the present oral dosage form does not comprise any enteric release material at all.

Generally, enteric release material can be regarded as a material which, when included in the oral dosage form, ensures the passage of the active pharmaceutical ingredient without substantial dissolution in the stomach. In other words, an enteric release material can be regarded as a material which forms a barrier to prevent the dissolution of the active pharmaceutical ingredient already under gastric conditions; i.e. the enteric release material can protect the active pharmaceutical ingredient form the acidity of the stomach.

Preferably, an enteric coating material or an enteric release material can be regarded as material which is substantially insoluble at a pH value of 5.5 or lower and/or which is substantially soluble at a pH value of 6.5 or higher.

Enteric release materials are for example methylcellulose, ethylcellulose, hydroxypropyl cellulose, hydroxypropyl methyl cellulose phthalate, hydroxypropyl methyl cellulose succinate, cellulose acetate phthalate, cellulose acetate succinate, cellulose trimellitate, alkyl (meth)acrylate-(meth) acrylate copolymers, carnauba wax, xanthan, gum, gelatin, chitosan, carrageenan, alginates.

In a preferred embodiment of the invention the oral dosage form of the present invention is free of an enteric coating. In is particularly preferred, that the oral dosage form is free of an enteric coating comprising one or more of methylcellulose, ethylcellulose, hydroxypropyl cellulose, hydroxypropyl methyl cellulose phthalate, hydroxypropyl methyl cellulose succinate, cellulose acetate phthalate, cellulose acetate succinate, cellulose trimellitate and alkyl (meth)acrylate-(meth)acrylate copolymers.

The oral dosage form of the invention can preferably have a water activity value of 0.3 to 1.0, preferably 0.4 to 0.9, in particular 0.5 to 0.8. Contrary to the content of water of a substance/oral dosage form, the activity of water is a measure for the "active" or "available" water of the substance/oral dosage form. The activity of water value ($a_w$) is defined as the ratio of the water vapor partial pressure of the substance (p) to the saturated vapor pressure of pure water ($p_0$) at a distinct temperature and thus can be calculated from the following equation:

$$a_w = p/p_0$$

The water activity value of the oral dosage form of the present invention can be preferably determined as described below in the experimental section.

In a preferred embodiment the oral dosage form of the present invention comprises:
- 60-95 wt % rifaximin (A), preferably 65-90 wt % rifaximin (A), in particular 70-85 wt % rifaximin (A),
- 5-30 wt % filler, preferably 12-28 wt % filler, in particular 15-25 wt % filler, e.g. microcrystalline cellulose,
- 0-10 wt % disintegrant, preferably 0.25-8 wt % disintegrant, in particular 0.5-5 wt % disintegrant, e.g. sodium carboxymethyl starch,
- 0-5 wt % lubricant, preferably 0.25-3.5 wt % lubricant, in particular 0.5-2.5 wt % lubricant, e.g. magnesium stearate,
- 0-5 wt % glidant, preferably 0.5-4 wt % glidant, in particular 0.75-3 wt % glidant, e.g. talc and/or colloidal silicon dioxide, wherein the wt. % are based on the total weight of the oral dosage form.

The oral dosage form of the present invention can preferably have a weight of 900 to 1200 mg, preferably 925 to 1150 mg. In an alternative preferred embodiment the tablet of the present invention can have a weight of 1000 to 1400 mg, preferably 1100 to 1350 mg, in particular 1150 to 1250 mg. The weight of the oral dosage form enables an administration by a simple dosage regime. The amount of 700-900 mg, preferably 800 mg, which is used to treat Crohn's disease, can preferably be administered all at once; i.e. for example by one single tablet or one capsule.

The oral dosage form can be preferably present as a capsule or tablet. In a preferred embodiment the oral dosage form is present in form of a tablet.

In case that the oral dosage form is a tablet, the tablet can preferably be coated or uncoated, preferably coated, more preferably film-coated, in particular film-coated with a film coating that does not affect the release of the active agent(s).

Preferred examples of film coatings which do not affect the release of the active ingredient can be formed of the coating material as described under pharmaceutical acceptable excipients.

In a preferred embodiment the film can have a thickness of 2 μm to 150 μm, preferably 10 to 100 μm, more preferably 20 to 60 μm.

The preferred coating may comprise a film-forming agent and one or more of the following: lubricant, surfactant, glidant, pigment and water.

It is further preferred that the oral dosage form of the invention, preferably a tablet, is kept at a water activity above 0.30, preferably above 0.40, in particular above 0.50.

In a preferred embodiment of the present invention the oral dosage form of the present invention is packed by a suitable packaging material. The packaging material preferably reduces or prevents water exchange between the oral dosage form of the present invention and the environment. For example, if the dosage form is a tablet or capsule, suitable blister pack materials can be used. The blister pack may comprise a cavity or pocket, preferably containing a thermoformed plastic. This usually has as a backing a lidding seal containing an aluminum and/or plastic foil. Further, if the composition is in form of a granulate, suitable sachets can be used.

In a particularly preferred embodiment the oral dosage form of the present invention is packed by a material having a water vapor permeability of 0.001 to 0.15 $g/m^2/day$ at 38° C./5%/90% RH, preferably of 0.01 to 0.12 $g/m^2/day$ at 38° C./5%/90% RH, in particular 0.05 to 0.10 $g/m^2/day$ at 38° C./5%/90% RH, wherein said water vapor permeability is determined according to ASTM F1249-13. Preferably, a Permatran-W Model 3/33 device is used. The measurement is preferably carried out at 38° C. Further, preferably the humidity in the dry chamber is 5% relative humidity (=RH), whereas the humidity in the wet chamber is 90% RH.

In a preferred embodiment the packaging material can preferably be selected from polyvinylchloride (PVC), polyvinylidenchloride (PVDC), polyethylene (PE), polypropylene (PP), polyethylenterephthalate (PET) polystyrol (PS), polyamide and alumina or combinations thereof.

In a preferred embodiment the packing material comprises layered sheets, which can be thermoformed, containing one or more layers. In a preferred embodiment the packing material can be a composite material, e.g. co-extruded composite material, e.g. a polyamide-alumina-polyvinyl chloride composite material, which is also referred to as Nylon®-Alu-PVC.

In a preferred embodiment the packaging material has a thickness of 1 μm to 1 mm. In case of a blister pack the thermoformed plastic pocket preferably has a thickness of 100 to 1000 μm, more preferably of 150 to 800 μm. Further, the backing foil usually has a thickness of 10 to 150 μm, more preferably from 15 to 100 μm.

A further subject of the present invention is a method for preparing an oral dosage form according to the invention comprising the steps of
(i) providing (A) rifaximin in polymorphic form β and (B) optionally one or more pharmaceutical excipient(s),
(ii) optionally granulating the mixture from step (i),
(iii) compressing the mixture from step (i) or the granules from step (ii) and optionally further pharmaceutical excipients to a tablet or filling the mixture from step (i) or the granules from step (ii) and optionally further pharmaceutical excipients into to a capsule,
(iv) optionally coating the tablet from step (iii) with a non-enteric coating.

As far as (A) rifaximin and (B) optionally one or more pharmaceutical excipient(s) are concerned for the present method, the same applies as to the before-mentioned oral dosage form.

In step (i) rifaximin (A) and optionally one or more pharmaceutical excipients (B) are provided.

It is preferred that rifaximin (A) and (B) optionally one or more further excipient(s) can be sieved. Further, rifaximin (A) and (B) optionally one or more further excipient(s) can preferably be blended in order to provide a composition having a homogenous distribution of rifaximin (A) and (B) optionally one or more further excipient(s). Blending can be carried out with conventional mixing devices, e.g. in a free-fall mixer. Blending can be carried out e.g. for 1 minute to 30 minutes, preferably for 2 minutes to less than 10 minutes.

It is further preferred that the blend of rifaximin (A) and (B) optionally one or more further excipient(s) can be sieved, preferably with a sieve having a mesh size of 25 to 1000 μm, preferably 50 to 800 μm, especially 100 to 600 μm.

In optional step (ii) the mixture from step (i) and optionally one or more further excipient(s) can be granulated. It is preferred that the method of the present invention comprises step (ii). In a preferred embodiment step (ii) comprises dry-granulating the mixture of step (i).

"Dry" is usually understood to mean that the step is carried out in the absence of a liquid, in particular in the absence of water. "Granulating" is generally understood to mean the formation of relatively coarse or granular aggregate material as a powder by assembling and/or aggregating finer powder particles (agglomerate formation or build-up granulation) and/or the formation of finer granules by breaking up coarser aggregates (disintegration or break-down granulation). Dry granulation can preferably be carried out by using pressure or temperature. In a preferred embodiment of the invention, step (ii) of granulating, preferably dry-granulating, the mixture from step (i) can be performed for example by "slugging" using a large heavy-duty rotary press and breaking up the slugs into granules with a hammer mill or by roller compaction using for example roller compactors by Powtec or Alexanderwerk. The granules are then optionally screened.

In step (iii) the mixture of step (i) or the granules of step (ii) and optionally further pharmaceuticals excipients can be compressed to a tablet. As far as the further pharmaceutical excipients in step (iii) are concerned the same as described above with regard to (B) one or more pharmaceutical excipient(s) applies. Compressing the mixture of step (i) or the granules from step (ii) into a tablet can preferably be carried out by compressing said formulation on a rotary press. The main compression force can range from 1 to 50 kN, preferably from 3 to 40 kN. The resulting tablets can have a hardness of 30 to 400 N, more preferably of 50 to 250 N, particularly preferably of 30 to 180 N, more preferably 40 to 150 N, wherein the hardness can be measured according to Ph. Eur. 6.0, Chapter 2.9.8.

Alternatively in step (iii) the mixture of step (i) or the granules of step (ii) and optionally further pharmaceuticals excipients can be filled into a capsule, preferably a hard gelatine capsule. For filling the mixture of step (i) or the granules of step (ii) into capsules dependent dosing systems (for example an auger) or preferably independent dosing systems (for example MG2, Matic (IMA)) can be used.

In a preferred embodiment steps (i), (ii) and (iii) can be performed under standard conditions, i.e. no specific care has to be taken with regard to humidity. In particular, these steps can be performed at a temperature from 00 to 30° C., preferably from 10 to 25° C. Further, said process is preferably performed at the humidity of 30 to 70% RH. The same conditions can be chosen for optional steps (iv) and (v) as described below.

Further, the dosage form, preferably the tablet, of the invention preferably has a content uniformity, i.e. a content of active agent(s) which lies within the concentration of 90 to 110%, preferably 95 to 105%, especially preferred from 98 to 102% of the average content of the active agent(s). The "content uniformity" is determined with a test in accordance with Ph. Eur., 6.0, Chapter 2.9.6. According to that test, the content of the active agent of each individual tablet out of 20 tablets must lie between 90 and 110%, preferably between 95 and 105%, especially between 98 and 102% of the average content of the active agent(s). Therefore, the content of the active agent in each tablet of the invention differs from the average content of the active agent by at most 10%, preferably at most 5% and especially at most 2%.

In addition, the resulting tablet preferably has a friability of less than 5%, particularly preferably less than 2%, especially less than 1%. The friability is determined in accordance with Ph. Eur., 6.0, Chapter 2.9.7. The friability of tablets generally refers to tablets without coating.

In an optional step (iv) the tablets from step (iii) can preferably be film coated, wherein it is preferred that a coating not affecting the release of the active pharmaceutical ingredient. Preferably a film coating such as Opadry II can be used.

In a further optional step (v) the tablets from step (iii) or optional step (iv) can be packaged. Preferably, the materials as described above are used.

The invention shall be illustrated by the following examples.

EXAMPLES

1. Analytical Methods
1.1 XPRD & Rietveld Refinement

Parameters XRPD: X-ray powder diffraction patterns (XRPD) were obtained with an X'Pert PRO diffractometer (PANalytical, Almelo, Netherlands) equipped with a theta/theta coupled goniometer in transmission geometry, programmable XYZ-stage with well plate holder, Cu-K$\alpha$1,2 radiation source (wavelength 0.15419 nm) with a focusing mirror, a 0.5° divergence slit, a 0.04 rad Soller slit collimator and a 0.5° anti-scattering slit on the incident beam side, a 1.4 mm anti-scattering slit, a 0.02 rad Soller slit collimator, a Ni-filter and a 1d-PIXcel solid state line detector (255 channels) on the diffracted beam side. The patterns were recorded at a tube voltage of 45 kV, tube current of 40 mA, applying a stepsize of 0.013° 2-theta with an exposure time of 40 s per step in the angular range of 2° to 40° 2-Theta at ambient conditions, preferably at 25° C. and 20% RH. A typical precision of the 2-Theta values is in the range of about ±0.2° 2-Theta. Thus a diffraction peak that appears at 6.6° 2-Theta can appear between 6.4 and 6.8° 2-Theta on most X-ray diffractometers under standard conditions.

Rietveld refinement of the sample's phase composition was done by Highscore 4.1 from Panalytical. Crystal structures were received from the Cambridge structural database as described in Braga et al., CrystEngComm, 2012, 14, 6404-6411. Atom positions are taken directly from single-crystal structure and are not refined; no correction is attempted for the fact that the single-crystal structures are measured at 25° C. An overall isotropic Debye-Waller factor was refined with the same value for all phases. Refined parameters are the zero point, scaling factors, lattice parameters, 5 background points, 3 peak-width parameters and 1 parameter of anisotropic broadening. Preferred orientation correction in hkl 1 1 0 is refined for the main phases with the 1-parameter March model.

1.2 Water Content According to Karl Fisher

The water content was determined according to Ph. Eur. 6.0, 2.5.12 Method A, wherein an Excellence Titrator T70 (Mettler Toledo) was used.

Preferably, the following measurement parameters can be used:
Weight sample: 200 mg
Density: 1.0 g/mL
Temperature: 25° C.
Titration agent: KF1-comp 5
Nominal concentration: 5 mg/mL
Weight 0.015 g
Temperature: 25° C.
Duration for mixing: 30 sec
Sensor type: polarised
Sensor DM 143-SC
Unit: mV
Indication voltametric
Ipol 24.0 µA
Stirring: 35%
Regulation:
Endpoint: 100.0 mV
Control band: 400.0 mV
Dosing rate (max): 5 mL/min
Dosing rate (min): 80 µL/min
Stop
Type: Drift stop absolute
Drift 25 µg/min
at Vmax: 50 mL
Time (min,) 0
Time (max.) ∞
Calculation
Result: Content
Result (unit) %
Formula: R1=(VEQ·CONC−TIME·DRIFT/1000)·C/m
Constant C=0.1

The sample is prepared and weighted in a glove box with less than 5% RH. For determination of the water content 5 samples were measured and the average from the corresponding values was calculated.

1.3 Water Activity

Determination of the relative humidity (in %) in the air above a specimen after establishment of the humidity equilibrium in a closed system at constant temperature with the following equipment:
Hygrometer: chamber Rotronic AW-VC and hygrometer BT-RS1
Temperature: 25±1° C.
Glove box: flushed with dry air or nitrogen, equipped with hygrometer, 5% RH
Procedure:

The sample dish was filled with the specimen and the sample dish was placed in the measuring chamber which had been thermostated to 25±1° C. Then, the measuring chamber was sealed. When equilibrium of the relative humidity was established (trend indication disappears), the corresponding value was determined.

2. Preparation of Tablets 2.1 Tablet According to the Invention

Rifaximin in polymorphic form β, microcrystalline cellulose, sodium carboxymethyl starch, magnesium stearate, highly dispersed silicon dioxide and talc were sieved, mixed together and blended for 15 minutes at 23 rpm in a "Heidolph Reax 2 Überkopfmischer". The mixture is dry granulated with a roller compactor and the resulting granules were compressed. The resulting composition, which can also be referred to as tablets cores, contains per unit

| | |
|---|---|
| Rifaximin in polymorphic form β (water content 9.1 wt %) | 880 mg |
| Microcrystalline cellulose | 231 mg |
| Sodium carboxymethyl starch | 41.0 mg |
| Magnesium stearate | 20.0 mg |
| Highly dispersed silicon dioxide | 14.0 mg |
| Talc | 14.0 mg |

As can be seen, the total weight of the composition comprising 800 mg rifaximin calculated on the basis of anhydrous rifaximin is 1200 mg. The resulting tablet cores were film coated with Opadry II 85F540027 (23 mg).

2.2. Reference Tablet

Gastro-resistant rifaximin-containing microgranules were prepared according to Example 1 of WO 2006/094737.

With reference to Example 4 of WO 2006/094737 tablet cores were prepared, wherein each tablet core has the following composition:

| | |
|---|---|
| Rifaximin gastro-resistant micogranules | 650.0 mg |
| Microcrystalline cellulose (Avicel PH101) | 24.31 mg |
| Sodium carboxymethyl cellulose | 34.95 mg |
| Magnesium stearate | 8.74 mg |

As can be seen, the total weight of the composition comprising 400 mg rifaximin calculated on the basis of anhydrous rifaximin is 718 mg. Further resulting tablet cores were film coated with a composition according to Table 4 of WO 2006/094737 (20 mg).

For preparing an oral dosage form based on the gastro-resistant microgranules according to WO 2006/094737, wherein said oral dosage form should comprise 800 mg rifaximin, a tablet having a total weight of over 1450 mg would be necessary.

3. Dissolution of the Tablets

Figure 4:
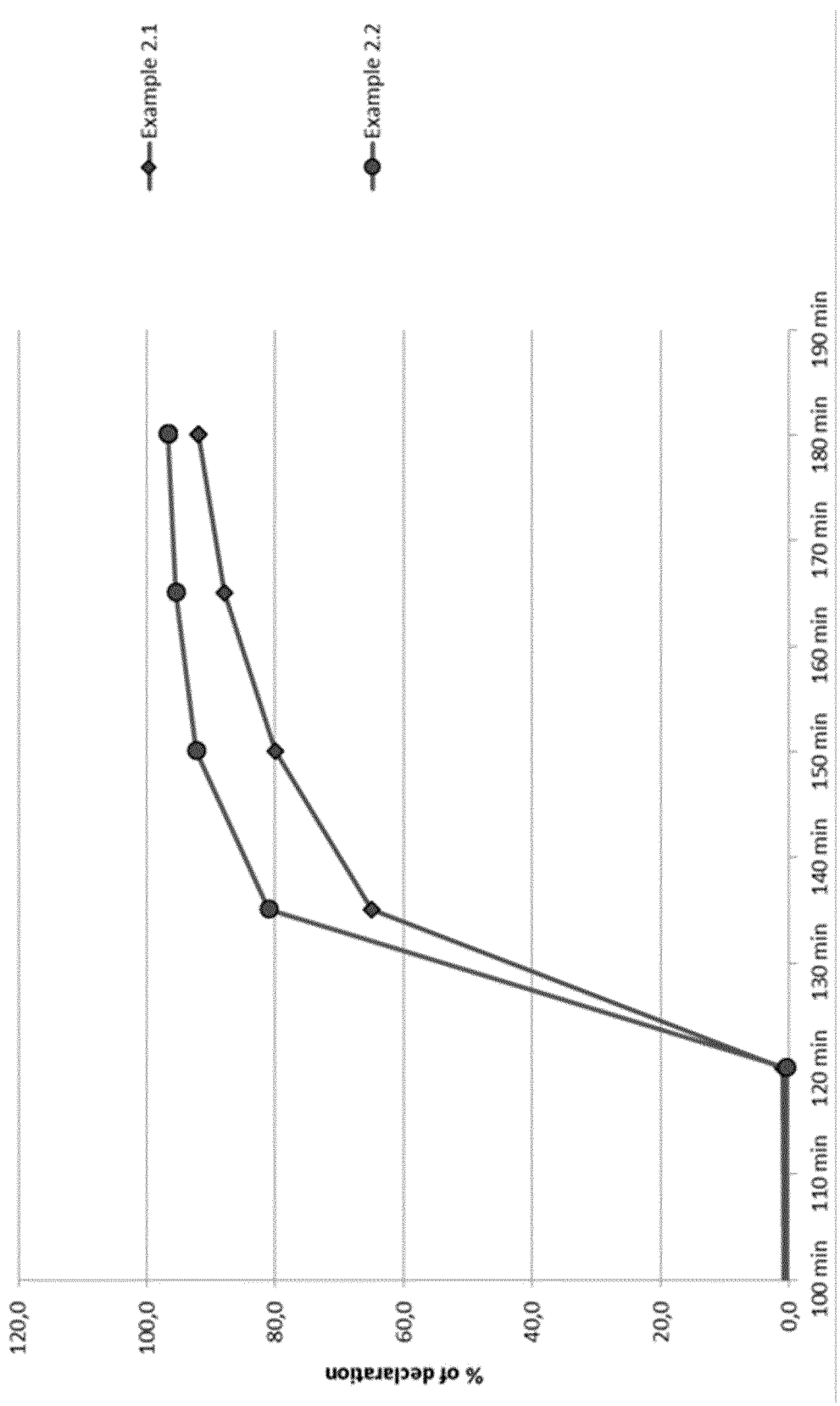
FIG. 4: Dissolution profiles from a tablet according to the invention and a reference tablet according to WO 2006/094737

Dissolution profiles of a tablet according to the present invention (Example 2.1) and a tablet according to WO 2006/094737 (Reference Example 2.2) were prepared. Dissolution is determined according to USP as before described. From FIG. 4 it can be derived that the present tablet, though not containing any enteric material, shows a dissolution profile being substantially the same as the tablet according to WO 2006/094737 containing significant amounts of enteric material.

The invention claimed is:

1. A tablet for delayed release comprising
   (A) 60 to 95 wt % of rifaximin in polymorphic form β, and
   (B) optionally one or more pharmaceutical excipient(s)
   wherein the rifaximin (A) contains 700-900 mg rifaximin calculated on the basis of anhydrous rifaximin, and
   wherein the tablet is free of enteric release material.

2. The tablet according to claim 1, wherein rifaximin in polymorphic form has diffraction peaks in the XRPD at 5.3, 6.9, 7.8, 10.4, 14.4 and 18.3 degrees 2θ (±0.2 degrees 2θ).

3. The tablet according to claim 1 being essentially free of other polymorphic forms of rifaximin.

4. The tablet according to claim 1 having a weight of 900 to 1200 mg.

5. The tablet according to claim 1 comprising:
   60-95 wt % rifaximin (A)
   5-30 wt % filler
   0-10 wt % disintegrant,
   0-5 wt % lubricant,
   0-5 wt % glidant,
   wherein the wt. % are based on the total weight of the tablet.

6. A method for preparing a tablet according to claim 1 comprising the steps of
   (i) providing (A) rifaximin in polymorphic form β and (B) optionally one or more pharmaceutical excipient(s)
   (ii) optionally granulating the mixture from step (i)
   (iii) compressing the mixture from step (i) or the granulates from step (ii) and optionally further pharmaceutical excipient(s) to a tablet
   (iv) optionally coating the tablet with a non-enteric coating.

7. The method according to claim 6, wherein step (ii) comprises dry granulating the mixture of step (i).

8. The method according to claim 7, wherein dry granulating the mixture of step (i) comprises compacting the mixture of step (i) to a slug and further granulating the slug.

9. The tablet according to claim 1, wherein the tablet comprises less than 5 mole percent of polymorphic form(s) of rifaximin other than form β, based on the total molar amount of rifaximin.

* * * * *